US009410209B2

(12) United States Patent
Robene et al.

(10) Patent No.: US 9,410,209 B2
(45) Date of Patent: Aug. 9, 2016

(54) **TEST FOR DETECTING *XANTHOMONAS AXONOPODIS* PV. *ALLII***

(75) Inventors: Isabelle Robene, Saint Gilles les Bains (FR); Olivier Pruvost, Tampon (FR); Delphine Legrand, Le Grau du Roi (FR)

(73) Assignee: Centre de Cooperation Internationale en Recherche Agronomique pour le Development (CIRAD), Paris (FR)

( * ) Notice: Subject to any disclaimer, the term of this patent is extended or adjusted under 35 U.S.C. 154(b) by 346 days.

(21) Appl. No.: 13/503,116

(22) PCT Filed: Oct. 21, 2010

(86) PCT No.: PCT/IB2010/054774
§ 371 (c)(1),
(2), (4) Date: Jul. 19, 2012

(87) PCT Pub. No.: WO2011/048569
PCT Pub. Date: Apr. 28, 2011

(65) Prior Publication Data

US 2013/0130239 A1 May 23, 2013

(30) Foreign Application Priority Data

Oct. 21, 2009 (FR) ...................................... 09 05053

(51) Int. Cl.
*C12Q 1/68* (2006.01)
*C12P 19/34* (2006.01)

(52) U.S. Cl.
CPC ................ *C12Q 1/689* (2013.01); *C12Q 1/686* (2013.01)

(58) Field of Classification Search
CPC ......... C12Q 1/689; C12Q 1/6895; C12R 1/64
See application file for complete search history.

(56) References Cited

PUBLICATIONS

Whalen et al. Avirulence gene avrRxv from Xanthomonas campestris pv. vesicatoria specifies resistance on tomato line Hawaii 7998. Molecular Plant-Microbe Interactions (1993) vol. 6, No. 5, pp. 616-627.*
Thieme et al. Insights into genome plasticity and pathogenicity of the plant pathogenic bacterium Xanthomonas campestris pv. vesicatoria revealed by the complete genome sequence. J. Bacteriology (2005) vol. 187, No. 21, pp. 7254-7266.*
Lowe et al. A computer program for selection of oligonucleotide primers for polymerase chain reactions. Nucleic Acids Res. (1990) vol. 18, No. 7, pp. 1757-1761.*
Hajri et al. A repertoire for repertoire hypothesis: repertoires of type three effectors are candidate determinants of host specificity in Xanthomonas. PLoS One (2009) vol. 4, issue 8, pp. 1-21.*
Picard, Polyphasic Characterization of Xanthomonas Axonopodis pv. allii Associated with Outbreaks of Bacterial Blight on Three Allium Species in the Mascarene Archipelago, Phytopathology, 98, pp. 919-925, 2008.
EMBL Database accession No. L20423, 1993.
Rademaker, Comparison of AFLP and rep-PCR Genomic Fingerprinting with DNA-DNA Homology Studies: Xanthomonas as a Model System, International Journal of Systematic and Evolutionary Microbiology, 50, pp. 665-677, 2000.
Whalen, Identification of a Host 14-3-3 Protein that Interacts with Xanthomonas Effector AvrRxv, Physiological and Molecular Plant Pathology, 72, pp. 46-55, 2008.
Bonshtien, Molecular Properties of the Xanthomonas AvrRxv Effector and Global Transcriptional Changes Determined by its Expression in Resistant Tomato Plants, Molecular Plant-Microbe Interactions, 18, pp. 300-310, 2005.

* cited by examiner

*Primary Examiner* — David Thomas
(74) *Attorney, Agent, or Firm* — Morgan, Lewis & Bockius LLP

(57) ABSTRACT

The present invention relates to novel tools for detecting *Xanthomonas axonopodis* pv. *allii*, in particular the molecular detection of specific polynucleotide sequences of said strain.

7 Claims, 5 Drawing Sheets

1 ATTATCCGCG CATTGTCGAC GGCGTGCATG CCGAAACGAA GTGCAGATGC GCTAGCCAAG
TAATAGGCGC GTAACAGCTG CCGCACGTAC GGCTTTGCTT CACGTCTACG CGATCGGTTC

61 CATAGCGCTC CATGGCACCG CCAAGCGGCA GTGCAAACAA CCGGTATGTC GACCCGAGGT
GTATCGCGAG GTACCGTGGC GGTTCGCCGT CACGTTTGTT GGCCATACAG CTGGGCTCCA

121 GTGCTGCGTC CAATGCGACT AATCCACGGC CGTGGCCCGG CTTTTTTGGG GTCGGTTAGT
CACGACGCAG GTTACGCTGA TTAGGTGCCG GCACCGGGCC GAAAAAACCC CAGCCAATCA

181 CACCGAACAT CAGTTGCGCA GATCACTCTT CAGTGTGAAT TAGTGTCGCT TATCTGTAGT
GTGGCTTGTA GTCAACGCGT CTAGTGAGAA GTCACACTTA ATCACAGCGA ATAGACATCA

241 GCTTCGTTCA GGGTTTTTCA GCTTTTCGCA TTATTGCCTA GATCTTCGCG CAACGAAACC
CGAAGCAAGT CCCAAAAAGT CGAAAAGCGT AATAACGGAT CTAGAAGCGC GTTGCTTTGG

301 GAGTTCTTCG ATTAGCGCGA TCTAATATAT GTGCGACTCC ATAAGAGTGC AATTCAGATC
CTCAAGAAGC TAATCGCGCT AGATTATATA CACGCTGAGG TATTCTCACG TTAAGTCTAG

361 CATACAAAAA ATGGTGGTAA AAAATGAAGA AATTTTTCAG ATCATTAGGA GTGGGCGGCT
GTATGTTTTT TACCACCATT TTTTACTTCT TTAAAAAGTC TAGTAATCCT CACCCGCCGA

PXaa2U
421 CAAGCAGCAG TCGTTTTCAA CATCATATTC CGGAGGCTGA CTCAGCACCC AGCAGTAAGG
GTTCGTCGTC AGCAAAAGTT GTAGTATAAG GCCTCCGACT GAGTCGTGGG TCGTCATTCC

481 CGTCTACGCC TCCGGCCTCT CCGCCGCCGG ATTCCCCGCC CAGTAACTCT GCTTTTTCCG
GCAGATGCGG AGGCCGGAGA GGCGGCGGCC TAAGGGGCGG GTCATTGAGA CGAAAAAGGC

541 CTCTCCCGAC AAGGCCTCGC AAGAAGGCCG AGGCCTTGTC GGATGCGGTG GAGTCGCGCG
GAGAGGGCTG TTCCGGAGCG TTCTTCCGGC TCCGGAACAG CCTACGCCAC CTCAGCGCGC

601 GACATTTAGC CCCGCCAAGC CTGGTCTCCT ATGCCAACGC AACCCTTGAT CAACTGAGGC
CTGTAAATCG GGGCGGTTCG GACCAGAGGA TACGGTTGCG TTGGGAACTA GTTGACTCCG

661 GAAATGAACC CATCAGCGAG TCACTTCGGC TGATGGACAT TGAAAATCTC CCCCATCTGG
CTTTACTTGG GTAGTCGCTC AGTGAAGCCG ACTACCTGTA ACTTTTAGAG GGGGTAGACC

721 TCCGCTCCTA CGACAATAGA TTGAATAATC TAAACCTGCG CAGCTTCGAC ACTCCGGGGC
AGGCGAGGAT GCTGTTATCT AACTTATTAG ATTTGGACGC GTCGAAGCTG TGAGGCCCCG

781 AGTTTTTACA TGACCTGAGT CGCTGGCATA AAACAGGATT GCCATTAAGA GCGGTAGTGC
TCAAAAATGT ACTGGACTCA GCGACCGTAT TTTGTCCTAA CGGTAATTCT CGCCATCACG

841 GGCTGGATGA AGACCCTAGG AGATGGCATC GCGTCGCGTT CGACGTGCGC AACCACGAGA
CCGACCTACT TCTGGGATCC TCTACCGTAG CGCAGCGCAA GCTGCACGCG TTGGTGCTCT

Figure 1a

901 GTGGACACAC GACGATTATC GCATTGGAGC CTGCGTCTGC TTACAATCCG GACCATATGC
CACCTGTGTG CTGCTAATAG CGTAACCTCG GACGCAGACG AATGTTAGGC CTGGTATACG

NXaa2U
961 CTGGTTTCGT GAAAATGAGA GAAAATCTCA CGTCTCAGTT CGGTAGGAAA ATTTCGTTTG
GACCAAAGCA CTTTTACTCT CTTTTAGAGT GCAGAGTCAA GCCATCCTTT TAAAGCAAAC

1021 CTGTGATTGA GGCGGAAGCA CTTAAGTCAA TCGGTGGGTG TGTCATATTT TCTCTTGATT
GACACTAACT CCGCCTTCGT GAATTCAGTT AGCCACCCAC ACAGTATAAA AGAGAACTAA

1081 ATGCCCTGGC GGCATACCAG GAAACAAGCA CCTTTGACCA ATGGCATAAA GATCTTCGAA
TACGGGACCG CCGTATGGTC CTTTCTTCGT GGAAACTGGT TACCGTATTT CTAGAAGCTT

1141 AGAAAGGAAA TATCAAGGGG ATGACTCCCG AAAGTCAGCA CCTTAACGAG CTTGGCGTCT
TCTTTCCTTT ATAGTTCCCC TACTGAGGGC TTTCAGTCGT GGAATTGCTC GAACCGCAGA

1201 ATTTGCTTAA AGGAACCAGG TTGCTGCCGG CAAACTTCTA CAAGCATGCG CATTCCAGGC
TAAACGAATT TCCTTGGTCC AACGACGGCC GTTTGAAGAT GTTCGTACGC GTAAGGTCCG

1261 GCACCATCGA CGAGCTCGAG GCAGATCAGC CTGGCGCGTC GGGTACCGAC GTGAGGTCAG
CGTGGTAGCT GCTCGAGCTC CGTCTAGTCG GACCGCGCAG CCCATGGCTG CACTCCAGTC

NXaa2L
1321 GCAGAGCCGC TGTCTACAAG GAGTCGCTGA GCCGTAGACT GGAGGAGTTC CAGGTCCAGC
CGTCTCGGCG ACAGATGTTC CTCAGCGACT CGGCATCTGA CCTCCTCAAG GTCCAGGTCG

PXaa2L
1381 GCGATAAGAC CTACAGCATG TCAATCGAAG CATCCAGAGC TCGAAAGATC CGTCACGCCT
CGCTATTCTG GATGTCGTAC AGTTAGCTTC GTAGGTCTCG AGCTTTCTAG GCAGTGCGGA

1441 TAGAATCCTG AGACAATTAC CAAATATTAT TTACTTTCCT TACCTTCACA GGCCCGCTTC
ATCTTAGGAC TCTGTTAATG GTTTATAATA AATGAAAGGA ATGGAAGTGT CCGGGCGAAG

1501 CCAGCGGGCT TTTTTTCGGT ATGTAATAAG GCGACCCTGA TGGAAAGCGC AACGGCAGGC
GGTCGCCCGA AAAAAAGCCA TACATTATTC CGCTGGGACT ACCTTTCGCG TTGCCGTCCG

1561 TTGTCGAATG AGGTTTGCTG TGTCTGAAGG GCTTGTCGCT ACGCCAGGCA GGATCATCCA
AACAGCTTAC TCCAAACGAC ACAGACTTCC CGAACAGCGA TGCGGTCCGT CCTAGTAGGT

1621 GTGGCAGCAG CTGCCGGCGC ATCGTGACAG ATACGAGAGC GCAAGCGACG TCAGCACTGG
CACCGTCGTC GACGGCCGCG TAGCACTGTC TATGCTCTCG CGTTCGCTGC AGTCGTGACC

1681 CGCCGTGTTC TTGGCCATGC CGCGAATCTG AACTTGGTGC AACCAACCTG ACGCTTGATC
GCGGCACAAG AACCGGTACG GCGCTTAGAC TTGAACCACG TTGGTTGGAC TGCGAACTAG

1741 GAGGTTCCTT AGCACACCGC AACATTGCGC GGCTGCGGGC GCCGCTGACG TGGGAAATCA
CTCCAAGGAA TCGTGTGGCG TTGTAACGCG CCGACGCCCG CGGCGACTGC ACCCTTTAGT

Figure 1b

```
1801    TCCGCTGCAC TGCGCTCGTT CACCTGGCAC ACGCGCGCAT CTGCGTCTAC CAGCGTTCGC
        AGGCGACGTG ACGCGAGCAA GTGGACCGTG TGCGCGCGTA GACGCAGATG GTCGCAAGCG

1861    GGTTGCTGCC GGGGCGTTTT CCAGCCTGCG CGGCGAGCCG GCAAGCTCGC CGCGCAGTGT
        CCAACGACGG CCCCGCAAAA GGTCGGACGC GCCGCTCGGC CGTTCGAGCG GCGCGTCACA

1921    TCAGTTGGCC AACGCCAGAT CCGTCAAC
        AGTCAACCGG TTGCGGTCTA GGCAGTTG
```

Figure 1c

Figure 2:
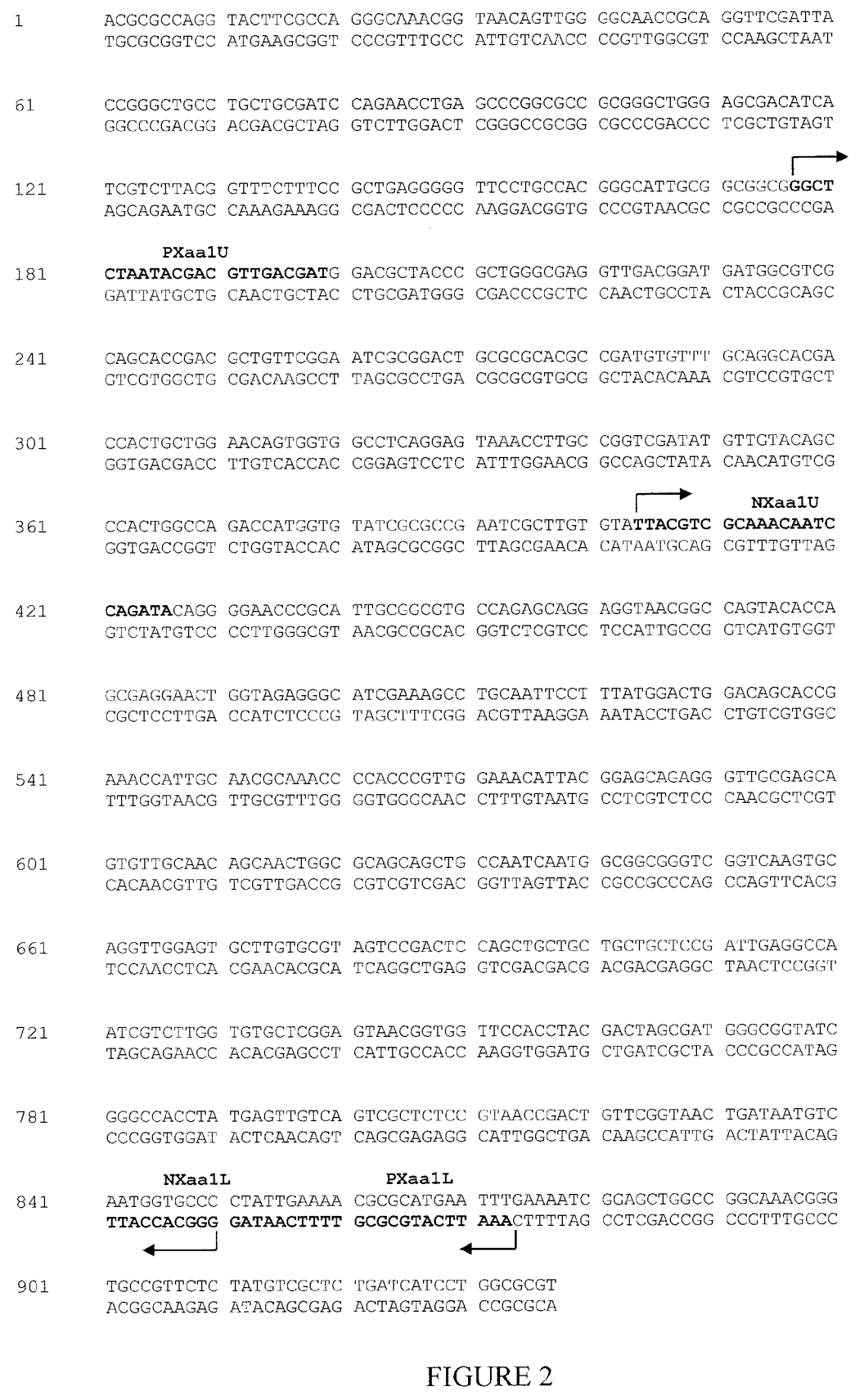

1 ACGCGCCAGG TACTTCGCCA GGGCAAACGG TAACAGTTGG GGCAACCGCA GGTTCGATTA
TGCGCGGTCC ATGAAGCGGT CCCGTTTGCC ATTGTCAACC CCGTTGGCGT CCAAGCTAAT

61 CCGGGCTGCC TGCTGCGATC CAGAACCTGA GCCCGGCGCC GCGGGCTGGG AGCGACATCA
GGCCCGACGG ACGACGCTAG GTCTTGGACT CGGGCCGCGG CGCCCGACCC TCGCTGTAGT

121 TCGTCTTACG GTTTCTTTCC GCTGAGGGGG TTCCTGCCAC GGGCATTGCG GCGGCGGGCT
AGCAGAATGC CAAAGAAAGG CGACTCCCCC AAGGACGGTG CCCGTAACGC CGCCGCCCGA

PXaa1U
181 CTAATACGAC GTTGACGATG GACGCTACCC GCTGGGCGAG GTTGACGGAT GATGGCGTCG
GATTATGCTG CAACTGCTAC CTGCGATGGG CGACCCGCTC CAACTGCCTA CTACCGCAGC

241 CAGCACCGAC GCTGTTCGGA ATCGCGGACT GCGCGCACGC CGATGTGTTT GCAGGCACGA
GTCGTGGCTG CGACAAGCCT TAGCGCCTGA CGCGCGTGCG GCTACACAAA CGTCCGTGCT

301 CCACTGCTGG AACAGTGGTG GCCTCAGGAG TAAACCTTGC CGGTCGATAT GTTGTACAGC
GGTGACGACC TTGTCACCAC CGGAGTCCTC ATTTGGAACG GCCAGCTATA CAACATGTCG

NXaa1U
361 CCACTGGCCA GACCATGGTG TATCGCGCCG AATCGCTTGT GTATTACGTC GCAAACAATC
GGTGACCGGT CTGGTACCAC ATAGCGCGGC TTAGCGAACA CATAATGCAG CGTTTGTTAG

421 CAGATACAGG GGAACCCGCA TTGCGGCGTG CCAGAGCAGG AGGTAACGGC CAGTACACCA
GTCTATGTCC CCTTGGGCGT AACGCCGCAC GGTCTCGTCC TCCATTGCCG GTCATGTGGT

481 GCGAGGAACT GGTAGAGGGC ATCGAAAGCC TGCAATTCCT TTATGGACTG GACAGCACCG
CGCTCCTTGA CCATCTCCCG TAGCTTTCGG ACGTTAAGGA AATACCTGAC CTGTCGTGGC

541 AAACCATTGC AACGCAAACC CCACCCGTTG GAAACATTAC GGAGCAGAGG GTTGCGAGCA
TTTGGTAACG TTGCGTTTGG GGTGGGCAAC CTTTGTAATG CCTCGTCTCC CAACGCTCGT

601 GTGTTGCAAC AGCAACTGGC GCAGCAGCTG CCAATCAATG GCGGCGGGTC GGTCAAGTGC
CACAACGTTG TCGTTGACCG CGTCGTCGAC GGTTAGTTAC CGCCGCCCAG CCAGTTCACG

661 AGGTTGGAGT GCTTGTGCGT AGTCCGACTC CAGCTGCTGC TGCTGCTCCG ATTGAGGCCA
TCCAACCTCA CGAACACGCA TCAGGCTGAG GTCGACGACG ACGACGAGGC TAACTCCGGT

721 ATCGTCTTGG TGTGCTCGGA GTAACGGTGG TTCCACCTAC GACTAGCGAT GGGCGGTATC
TAGCAGAACC ACACGAGCCT CATTGCCACC AAGGTGGATG CTGATCGCTA CCCGCCATAG

781 GGGCCACCTA TGAGTTGTCA GTCGCTCTCC GTAACCGACT GTTCGGTAAC TGATAATGTC
CCCGGTGGAT ACTCAACAGT CAGCGAGAGG CATTGGCTGA CAAGCCATTG ACTATTACAG

NXaa1L PXaa1L
841 AATGGTGCCC CTATTGAAAA CGCGCATGAA TTTGAAAATC GGAGCTGGCC GGCAAACGGG
TTACCACGGG GATAACTTTT GCGCGTACTT AAACTTTTAG CCTCGACCGG CCGTTTGCCC

901 TGCCGTTCTC TATGTCGCTC TGATCATCCT GGCGCGT
ACGGCAAGAG ATACAGCGAG ACTAGTAGGA CCGCGCA

SEQUENCE LISTING

```
<160> NUMBER OF SEQ ID NOS: 20

<210> SEQ ID NO 1
<211> LENGTH: 23
<212> TYPE: DNA
<213> ORGANISM: Artificial
<220> FEATURE:
<223> OTHER INFORMATION: Primer Pxaa1U

<400> SEQUENCE: 1

ggctctaata cgacgttgac gat                                              23


<210> SEQ ID NO 2
<211> LENGTH: 23
<212> TYPE: DNA
<213> ORGANISM: Artificial
<220> FEATURE:
<223> OTHER INFORMATION: Primer Pxaa1L

<400> SEQUENCE: 2

aaattcatgc gcgttttcaa tag                                              23


<210> SEQ ID NO 3
<211> LENGTH: 23
<212> TYPE: DNA
<213> ORGANISM: Artificial
<220> FEATURE:
<223> OTHER INFORMATION: Primer Nxaa1U

<400> SEQUENCE: 3

ttacgtcgca aacaatccag ata                                              23


<210> SEQ ID NO 4
<211> LENGTH: 23
<212> TYPE: DNA
<213> ORGANISM: Artificial
<220> FEATURE:
<223> OTHER INFORMATION: Primer Nxaa1L

<400> SEQUENCE: 4

gggcaccatt gacattatca gtt                                              23


<210> SEQ ID NO 5
<211> LENGTH: 937
<212> TYPE: DNA
<213> ORGANISM: Xanthomonas axonopodis

<400> SEQUENCE: 5

acgcgccagg tacttcgcca gggcaaacgg taacagttgg ggcaaccgca ggttcgatta      60

ccgggctgcc tgctgcgatc cagaacctga gcccggcgcc gcgggctggg agcgacatca     120
```

-continued

```
tcgtcttacg gtttctttcc gctgaggggg ttcctgccac gggcattgcg gcggcgggct    180
ctaatacgac gttgacgatg gacgctaccc gctgggcgag gttgacggat gatggcgtcg    240
cagcaccgac gctgttcgga atcgcggact gcgcgcacgc cgatgtgttt gcaggcacga    300
ccactgctgg aacagtggtg gcctcaggag taaaccttgc cggtcgatat gttgtacagc    360
ccactggcca gaccatggtg tatcgcgccg aatcgcttgt gtattacgtc gcaaacaatc    420
cagatacagg ggaacccgca ttgcggcgtg ccagagcagg aggtaacggc cagtacacca    480
gcgaggaact ggtagagggc atcgaaagcc tgcaattcct ttatggactg gacagcaccg    540
aaaccattgc aacgcaaacc ccacccgttg gaaacattac ggagcagagg gttgcgagca    600
gtgttgcaac agcaactggc gcagcagctg ccaatcaatg gcggcgggtc ggtcaagtgc    660
aggttggagt gcttgtgcgt agtccgactc cagctgctgc tgctgctccg attgaggcca    720
atcgtcttgg tgtgctcgga gtaacggtgg ttccacctac gactagcgat gggcggtatc    780
gggccaccta tgagttgtca gtcgctctcc gtaaccgact gttcggtaac tgataatgtc    840
aatggtgccc ctattgaaaa cgcgcatgaa tttgaaaatc ggagctggcc ggcaaacggg    900
tgccgttctc tatgtcgctc tgatcatcct ggcgcgt                             937
```

<210> SEQ ID NO 6
<211> LENGTH: 1948
<212> TYPE: DNA
<213> ORGANISM: Xanthomonas axonopodis

<400> SEQUENCE: 6

```
attatccgcg cattgtcgac ggcgtgcatg ccgaaacgaa gtgcagatgc gctagccaag     60
catagcgctc catggcaccg ccaagcggca gtgcaaacaa ccggtatgtc gacccgaggt    120
gtgctgcgtc caatgcgact aatccacggc cgtggcccgg ctttttttggg gtcggttagt    180
caccgaacat cagttgcgca gatcactctt cagtgtgaat tagtgtcgct tatctgtagt    240
gcttcgttca gggtttttca gcttttcgca ttattgccta gatcttcgcg caacgaaacc    300
gagttcttcg attagcgcga tctaatatat gtgcgactcc ataagagtgc aattcagatc    360
catacaaaaa atggtggtaa aaaatgaaga aatttttcag atcattagga gtgggcggct    420
caagcagcag tcgttttcaa catcatattc cggaggctga ctcagcaccc agcagtaagg    480
cgtctacgcc tccggcctct ccgccgccgg attccccgcc cagtaactct gctttttccg    540
ctctcccgac aaggcctcgc aagaaggccg aggccttgtc ggatgcggtg gagtcgcgcg    600
gacatttagc ccgcgccaagc ctggtctcct atgccaacgc aaccccttgat caactgaggc    660
gaaatgaacc catcagcgag tcacttcggc tgatggacat tgaaaatctc cccatctgg    720
tccgctccta cgacaataga ttgaataatc taaacctgcg cagcttcgac actccggggc    780
agtttttaca tgacctgagt cgctggcata aaacaggatt gccattaaga gcggtagtgc    840
ggctggatga agaccctagg agatggcatc gcgtcgcgtt cgacgtgcgc aaccacgaga    900
gtggacacac gacgattatc gcattggagc ctgcgtctgc ttacaatccg gaccatatgc    960
ctggtttcgt gaaaatgaga gaaaatctca cgtctcagtt cggtaggaaa atttcgtttg   1020
ctgtgattga ggcggaagca cttaagtcaa tcggtgggtg tgtcatattt tctcttgatt   1080
atgccctggc ggcataccag gaaagaagca cctttgacca atggcataaa gatcttcgaa   1140
agaaaggaaa tatcaagggg atgactcccg aaagtcagca ccttaacgag cttggcgtct   1200
atttgcttaa aggaaccagg ttgctgccgg caaacttcta caagcatgcg cattccaggc   1260
```

-continued

```
gcaccatcga cgagctcgag gcagatcagc ctggcgcgtc gggtaccgac gtgaggtcag   1320

gcagagccgc tgtctacaag gagtcgctga gccgtagact ggaggagttc caggtccagc   1380

gcgataagac ctacagcatg tcaatcgaag catccagagc tcgaaagatc cgtcacgcct   1440

tagaatcctg agacaattac caaatattat ttactttcct taccttcaca ggcccgcttc   1500

ccagcgggct ttttttcggt atgtaataag gcgaccctga tggaaagcgc aacggcaggc   1560

ttgtcgaatg aggtttgctg tgtctgaagg gcttgtcgct acgccaggca ggatcatcca   1620

gtggcagcag ctgccggcgc atcgtgacag atacgagagc gcaagcgacg tcagcactgg   1680

cgccgtgttc ttggccatgc cgcgaatctg aacttggtgc aaccaacctg acgcttgatc   1740

gaggttcctt agcacaccgc aacattgcgc ggctgcgggc gccgctgacg tgggaaatca   1800

tccgctgcac tgcgctcgtt cacctggcac acgcgcgcat ctgcgtctac cagcgttcgc   1860

ggttgctgcc ggggcgtttt ccagcctgcg cggcgagccg gcaagctcgc cgcgcagtgt   1920

tcagttggcc aacgccagat ccgtcaac                                       1948


<210> SEQ ID NO 7
<211> LENGTH: 21
<212> TYPE: DNA
<213> ORGANISM: Artificial
<220> FEATURE:
<223> OTHER INFORMATION: Primer Pxaa2U

<400> SEQUENCE: 7

ctcaagcagc agtcgttttc a                                                21


<210> SEQ ID NO 8
<211> LENGTH: 21
<212> TYPE: DNA
<213> ORGANISM: Artificial
<220> FEATURE:
<223> OTHER INFORMATION: Primer Pxaa2L

<400> SEQUENCE: 8

atgcttcgat tgacatgctg t                                                21


<210> SEQ ID NO 9
<211> LENGTH: 17
<212> TYPE: DNA
<213> ORGANISM: Artificial
<220> FEATURE:
<223> OTHER INFORMATION: Primer Nxaa2U

<400> SEQUENCE: 9

atgcctggtt tcgtgaa                                                     17


<210> SEQ ID NO 10
<211> LENGTH: 17
<212> TYPE: DNA
<213> ORGANISM: Artificial
<220> FEATURE:
<223> OTHER INFORMATION: Primer Nxaa2L

<400> SEQUENCE: 10

ctacggctca gcgactc                                                     17


<210> SEQ ID NO 11
<211> LENGTH: 10
<212> TYPE: DNA
<213> ORGANISM: Artificial
<220> FEATURE:
<223> OTHER INFORMATION: Primer 80-21
```

<400> SEQUENCE: 11
acgcgccagg 10

<210> SEQ ID NO 12
<211> LENGTH: 18
<212> TYPE: DNA
<213> ORGANISM: Artificial
<220> FEATURE:
<223> OTHER INFORMATION: Primer PSAC

<400> SEQUENCE: 12
tagactgcgt acaagctc 18

<210> SEQ ID NO 13
<211> LENGTH: 16
<212> TYPE: DNA
<213> ORGANISM: Artificial
<220> FEATURE:
<223> OTHER INFORMATION: Primer PMSP

<400> SEQUENCE: 13
gatgagtcct gagcgg 16

<210> SEQ ID NO 14
<211> LENGTH: 16
<212> TYPE: DNA
<213> ORGANISM: Artificial
<220> FEATURE:
<223> OTHER INFORMATION: Primer MSPI

<400> SEQUENCE: 14
gatgagtcct gagcgg 16

<210> SEQ ID NO 15
<211> LENGTH: 19
<212> TYPE: DNA
<213> ORGANISM: Artificial
<220> FEATURE:
<223> OTHER INFORMATION: Primer SacI+ C

<400> SEQUENCE: 15
tagactgcgt acaagctcc 19

<210> SEQ ID NO 16
<211> LENGTH: 20
<212> TYPE: DNA
<213> ORGANISM: Artificial
<220> FEATURE:
<223> OTHER INFORMATION: Primer SacI+CT

<400> SEQUENCE: 16
tagactgcgt acaagctcct 20

<210> SEQ ID NO 17
<211> LENGTH: 19
<212> TYPE: DNA
<213> ORGANISM: Artificial
<220> FEATURE:
<223> OTHER INFORMATION: Primer F1154

<400> SEQUENCE: 17
gaccatatgc ctggtttcg 19

<210> SEQ ID NO 18

-continued

```
<211> LENGTH: 20
<212> TYPE: DNA
<213> ORGANISM: Artificial
<220> FEATURE:
<223> OTHER INFORMATION: Primer R1391

<400> SEQUENCE: 18

ccttaaggtg ctgactttcg                                              20


<210> SEQ ID NO 19
<211> LENGTH: 18
<212> TYPE: DNA
<213> ORGANISM: Artificial
<220> FEATURE:
<223> OTHER INFORMATION: Primer F202

<400> SEQUENCE: 19

attatccgcg cattgtcg                                                18


<210> SEQ ID NO 20
<211> LENGTH: 19
<212> TYPE: DNA
<213> ORGANISM: Artificial
<220> FEATURE:
<223> OTHER INFORMATION: Primer R2149

<400> SEQUENCE: 20

gttgacggat ctggcgttg                                               19
```

TEST FOR DETECTING *XANTHOMONAS AXONOPODIS* PV. *ALLII*

RELATED APPLICATIONS

The present application is a U.S. National Phase Application of International Application No. PCT/IB2010/054774 (filed Oct. 21, 2010) which claims priority to French Application No. 0905053 (filed Oct. 21, 2009) which are hereby incorporated by reference in their entirety.

SEQUENCE LISTING SUBMISSION VIA EFS-WEB

A computer readable text file, entitled "045636-5192_SequenceListing.txt," created on or about Apr. 18, 2012, with a file size of about 8 kb contains the sequence listing for this application and is hereby incorporated by reference in its entirety.

The present invention relates to novel tools for detecting *Xanthomonas axonopodis* pv. *allii.*

*Xanthomonas axonopodis* pv. *allii* is the agent responsible for bacterial blight of onion, one of the major health constraints in the cultivation of Alliaceae. This disease was observed for the first time in 1971 in Barbados (West Indies), then in 1975 in several islands of the Hawaiian archipelago. In the 1980s, this bacterium was found in Brazil, in Cuba and in Mauritius. Between 1990 and 2000, it reached the United States, Venezuela, South Africa and Japan, causing considerable damage. *Xanthomonas axonopodis* pv. *allii* was characterized for the first time in Hawaii in 1978 (Alvarez et al., Physiopathology; 68: 1132-1136, 1978).

*Xanthomonas axonopodis* pv. *allii* is pathogenic for Alliaceae, in particular garlic, leek, chive shallot and onion (Roumagnac et al., Int. J. Syst. Evol. Microbiol., 54: 15-24, 2004), the disease tending to be more severe in onion. This bacterium has also proven to be pathogenic for species of the *Citrus* genus during experimental infections by infiltration (Gent et al., Phytopathology, 95(8): 918-925, 2005); there is, however, no evidence showing that this bacterium is pathogenic in the field for the *Citrus* genus.

In onion, *Xanthomonas axonopodis* pv. *allii* causes lesions on the aerial tissues of the plant (leaves and floral scapes), characterized by the presence of small lenticular watersoaked spots which spread and progress rapidly into chlorosis then necrosis. The disease is promoted by high temperatures (above 27° C.) and large foci occur rapidly (7 to 10 days) after a period of humid and rainy weather. Because of the reduction in foliage, the plants shrivel up and the bulbs diminish, thereby leading to considerable yield losses, of about from 10 to 50%. For example, in the United States, yield losses of 20% or more are commonly observed in infected fields.

It has been shown that the bacterium can be present in the onion seeds (Roumagnac et al., Eur. J. Plant Pathol., 106: 867-877, 2000), that the disease can spread on a large scale, in particular through commercial seed exchanges, and that 4 infected seeds out of 10 000 is sufficient to trigger an epidemic (Roumagnac et al., Phytopathology, 94: 138-146, 2004).

Within crops, wind and irrigation, and in particular irrigation through sprinklers, can provide greater dissemination of the disease, as is also the case with storms and hail. In addition, the bacterium is capable of surviving on crop debris which is then disseminated by adhering to workers' clothing and to equipment.

Owing to the size of the epidemics and the small proportion of contaminated seeds necessary to trigger sizeable epidemics, this bacterium was placed on the alert list of the European Plant Protection Organization (EPPO) in 2006. A procedure is ongoing for it to be included in the Al list of EPPO quarantine organisms.

Measures for combating bacterial blight of onion are available, for example the use of healthy seeds, the destruction of self-sown onions, the destruction of plant debris, rotations, chemical control.

In addition, international marketing and exchange of seeds are the main agents for the spread of this disease and represent a risk of introduction of the pathogenic agent into healthy regions or of introduction of new genotypes into regions already contaminated. It is therefore necessary to be able to guarantee the good health quality of these seeds. To do this, rapid, reliable and sensitive diagnostic tests which make it possible to routinely certify *Allium* seed lots are essential. At the current time, such diagnostic tools do not exist. The identification methods currently used are based on isolating the bacterium from the infected plant material and culturing it on a suitable medium, in particular NCTM1 medium (Roumagnac et al., Eur. J. Plant Pathol., 106: 867-877, 2000). The isolation of the bacterium takes several days, and the identity of the bacterium must then be verified by biochemical methods, molecular typing and/or pathogenicity tests (Gent et al., Phytopathology, 94(2): 184-195, 2004; Picard et al., Phytopathology, 98(9): 919-925, 2008). Furthermore, the presence of other bacteria in the samples can in certain cases reduce the sensitivity of the test and cause the detection of false positives.

A test for identification by PCR amplification of a specific sequence of *Xanthomonas axonopodis* pv. *allii* has been developed (Humeau et al., Phytopathology, 96(12): 1345-1354, 2006; Picard et al., Phytopathology, 98(9): 919-925, 2008). This test consists in carrying out a nested PCR using, in a first amplification step, the primers PXaa1U (SEQ ID NO: 1)/PXaa1L (SEQ ID NO: 2), then, in a second step, the primers NXaa1U (SEQ ID NO: 3)/NXaa1L (SEQ ID NO: 4). However, although this method is sensitive and reliable, it does not allow the detection of all strains, in particular those originating from Barbados and Brazil. The fault in detection of certain strains would be explained by the strong intra-pathovar genetic diversity in *Xanthomonas axonopodis* pv. *allii* (Picard et al., Phytopathology, 98(9): 919-925, 2008; Gent et al., Phytopathology, 94(2): 184-195, 2004; Gent et al., Phytopathology, 95(8): 918-925, 2005). In addition, a study of genetic diversity has shown that the polymorphism of the strains is variable depending on their geographic origin: there are strong-diversity regions (in particular the United States, South Africa) and weak-diversity regions (for example, Venezuela, Hawaii, Barbados).

Consequently, since no test is today available for detecting all of the *Xanthomonas axonopodis* pv. *allii* strains, the development of a reliable, sensitive diagnostic tool which allows the detection of all the strains, regardless of their geographic origin, is essential in order to optimize the combating of diseases caused by this bacterium and to improve health monitoring during international exchanges.

The inventors have now identified two target DNA sequences specific for *Xanthomonas axonopodis* pv. *allii.* These target sequences, called "PIL" and "AVR", are represented in the appended sequence listing under numbers SEQ ID NO: 5 and SEQ ID NO: 6, respectively.

The PIL marker, demonstrated by the Random Amplification of Polymorphic DNA, or RAPD, technique, is present in approximately 70% of *Xanthomonas axonopodis* pv. *allii* strains. It has been found that the primers PXaa1U (SEQ ID NO: 1)/PXaa1L (SEQ ID NO: 2) and NXaa1U (SEQ ID NO:

3)/NXaa1L (SEQ ID NO: 4) used by Humeau et al. (Phytopathology, 96: 1345-1354, 2006) hybridize to this target sequence.

The "AVR" marker, identified by the AFLP (for Amplified Fragment Length Polymorphism) method, is at least present in all the strains which do not have the "PIL" marker.

Thus, owing to the complementarity of these markers, the joint search for said markers allows selective diagnosis of all the known strains of *Xanthomonas axonopodis* pv. *allii.*

A subject of the present invention is therefore an isolated polynucleotide which can be obtained from *Xanthomonas axonopodis* pv. *allii*, characterized in that it is chosen from the group made up of:

a) the polynucleotide of sequence SEQ ID NO: 6;

b) a polynucleotide having 85%, preferably 90%, and more preferentially 95% identity with the sequence SEQ ID NO: 6;

c) any fragment of at least 15 bp of said polynucleotide;

d) any polynucleotide complementary to one of the polynucleotides a) or b);

e) any polynucleotide capable of selectively hybridizing, under stringent conditions, with one of the polynucleotides a), b), c) or d).

The identity percentages to which reference is made in the context of the disclosure of the present invention are determined on an overall alignment of the sequences to be compared, using the Needleman and Wunsch algorithm (J. Mol. Biol. 48, 443-453, 1970). This sequence comparison can be carried out, for example, using the "Geneious" alignment software (Drummond A J, Ashton B, Cheung M, Heled J, Kearse M, Moir R, Stones-Havas S, Thierer T, Wilson A; 2009, Geneious v 4.7).

Stringent hybridization conditions, for a given polynucleotide, can be identified by those skilled in the art according to the size and the base composition of the polynucleotide concerned, and also to the composition of the hybridization mixture (in particular, pH and ionic strength). Generally, stringent conditions, for a polynucleotide of given size and given sequence, are obtained by working at a temperature approximately 5° C. to 10° C. below the melting temperature (Tm) of the hybrid formed, in the same reaction mixture, by this polynucleotide and the polynucleotide complementary thereto.

The present invention encompasses in particular polynucleotides which can be used as amplification primers for obtaining a nucleic acid sequence in accordance with the invention, or as nucleic acid probes for detecting said sequence.

It encompasses in particular the pairs of primers which can be used for amplifying a polynucleotide of sequence SEQ ID NO: 6, or a fragment thereof.

By way of nonlimiting examples of pairs of primers in accordance with the invention, mention will in particular be made of:

- the pair of primers made up of the polynucleotides PXaa2U (SEQ ID NO: 7) and PXaa2L (SEQ ID NO: 8), which allows the amplification of a 995 bp fragment of the sequence SEQ ID NO: 6;
- the pair of primers made up of the polynucleotides NXaa2U (SEQ ID NO: 9) and NXaa2L (SEQ ID NO: 10), which allows the amplification of a 401 bp fragment of the sequence SEQ ID NO: 6.

FIG. 1 represents the sequence SEQ ID NO: 6. The sequence fragments in bold delimit the primers PXaa2U, PXaa2L, NXaa2U and NXaa2L.

Another subject of the present invention is the use of nucleic acid molecules in accordance with the invention for screening for *Xanthomonas axonopodis* pv. *allii*, and in particular the strains which do not comprise the "PIL" marker.

A subject of the present invention is also a method of screening for *Xanthomonas axonopodis* pv. *allii*, characterized in that it comprises:

- bringing DNA of a biological sample that may contain said bacterium into contact with one or more polynucleotide(s) in accordance with the invention, under conditions which allow selective hybridization between said polynucleotide(s) and the target sequence SEQ ID NO: 6, if said sequence is present in said DNA;
- detecting said hybridization.

The biological sample used may be either a culture of bacteria isolated from the plant or from the seeds of Alliaceae on which it is desired to carry out the detection, or directly the potentially infected seeds of Alliaceae, or a sample of the potentially infected plant. Advantageously, the detection is carried out on onion seeds.

The detection of the hybridization can be carried out by any means known in themselves to those skilled in the art. When a polynucleotide in accordance with the invention, labeled beforehand with a suitable label, is used as nucleic acid probe, the hybridization of the target sequence with the labeled probe is detected directly.

When two polynucleotides, constituting a pair of primers in accordance with the invention, are used, the hybridization of the primers with the target sequence is demonstrated by means of a polymerase chain reaction (PCR) amplification, and then by detection of the amplification product, in particular on agarose gel.

In this case, the screening method in accordance with the invention comprises at least the following steps:

i) bringing the DNA of a biological sample to be tested into contact with a pair of primers in accordance with the invention, under conditions which allow selective hybridization between the primers and the target sequence SEQ ID NO: 6;

ii) carrying out a polymerase chain reaction amplification under conditions which allow the amplification of the target sequence SEQ ID NO: 6;

iii) detecting the amplification product.

Preferably, the detection is carried out by nested PCR. In this embodiment of the invention, the screening method in accordance with the invention also comprises a second PCR amplification step (step iv) carried out using a second pair of primers allowing the amplification of an internal fragment of the amplification product from the first step.

By way of example, the first amplification step (step ii) of the method in accordance with this embodiment can be carried out using the pair of primers made up of the polynucleotides PXaa2U (SEQ ID NO: 7) and PXaa2L (SEQ ID NO: 8), and the second amplification step (step iv) using the pair of primers made up of the polynucleotides NXaa2U (SEQ ID NO: 9) and NXaa2L (SEQ ID NO: 10).

In order to be able to detect all the *Xanthomonas axonopodis* pv. *allii* strains, i.e. the strains which contain the "PIL" and "AVR" markers, and those which contain only one of these two markers, another particularly advantageous embodiment of the present method allows the detection of the target sequence SEQ ID NO: 5 ("PIL" marker) in addition to that of SEQ ID NO: 6 ("AVR" marker).

In this particular embodiment, one or more polynucleotide(s) in accordance with the invention capable of selectively hybridizing with the target sequence SEQ ID NO: 6, and one or more polynucleotide(s) capable of selectively hybridizing, under stringent conditions, with the target sequence SEQ ID NO: 5, are used.

When the method of detection according to the invention comprises a PCR amplification step, pairs of primers which allow the amplification of a polynucleotide of sequence SEQ ID NO: 5, or of a fragment thereof, and primers in accordance with the invention which allow the amplification of a polynucleotide of sequence SEQ ID NO: 6, or of a fragment thereof, are used.

In this case, in step i) of the method in accordance with the invention, the DNA of the sample is also brought into contact with one or more polynucleotide(s) capable of selectively hybridizing, under stringent conditions, with the target sequence SEQ ID NO: 5, and the conditions of step ii) allow, in addition to the amplification of the target sequence SEQ ID NO: 6, the amplification of the target sequence SEQ ID NO: 5.

Preferably, the pairs of primers that can be used for amplifying the polynucleotide of sequence SEQ ID NO: 5 are:

- the pair of primers PXaa1U (SEQ ID NO: 1) and PXaa1L (SEQ ID NO: 2), which allows the amplification of a 694 bp fragment of the sequence SEQ ID NO: 5; and
- the pair of primers NXaa1U (SEQ ID NO: 3) and NXaa1L (SEQ ID NO: 4), which allows the amplification of a 444 bp fragment of the sequence SEQ ID NO: 5.

FIG. 2 represents the sequence SEQ ID NO: 5. The sequence fragments in bold delimit the primers PXaa1U, PXaa1L, NXaa1U and NXaa1L.

When it is a question of a method of detection according to the invention comprising two amplification steps ("nested PCR" embodiment), a pair of primers allowing the amplification of all or part of the polynucleotide of sequence SEQ ID NO: 5 is used in the first amplification step (step ii)), in addition to the pair of primers according to the invention allowing the amplification of all or part of the polynucleotide of sequence SEQ ID NO: 6. In the second PCR amplification step (step iv), a pair of primers allowing the amplification of an internal fragment of the product of amplification of the sequence SEQ ID NO: 5 obtained in the first step is used, in addition to the primers according to the invention making it possible to amplify an internal fragment of the product of amplification of the sequence SEQ ID NO: 6.

In one particularly advantageous embodiment of the method according to the invention, the amplification step ii) is carried out with the pair of primers PXaa1U (SEQ ID NO: 1) and PXaa1L (SEQ ID NO: 2) and the pair of primers PXaa2U (SEQ ID NO: 7) and PXaa2L (SEQ ID NO: 8), and the amplification step iv) is carried out with the pair of primers NXaa1U (SEQ ID NO: 3) and NXaa1L (SEQ ID NO: 4) and the pair of primers NXaa2U (SEQ ID NO: 9) and NXaa2L (SEQ ID NO: 10). This embodiment has a sensitivity threshold of approximately 1 contaminated seed out of 27 300: it is therefore particularly reliable for evaluating the state of health of a sample of seeds, and it can be used for the certification of Alliaceae seeds, since the rate of seed contamination recorded for epidemics of bacterial blight of onion in the tropical environment is 4.5/10 000.

The embodiments of the method according to the invention targeting both the "PIL" and "AVR" target genes have the advantage of being able to detect all the *Xanthomonas axonopodis* pv. *allii* strains, as has been demonstrated by the inventors on a "worldwide collection", listed in table I (cf. hereinafter example 2.1), made up of 87 strains originating from various regions of the world, whereas most of the *Xanthomonas* strains different than the *Xanthomonas axonopodis* pv. *allii* pathovar are not detected. Only a few strains classified in genetic subgroups 9.1 and 9.2 of *Xanthomonas axonopodis*, which are not pathogenic for onion, are also detected. However, the latter can be easily distinguished from the *Xanthomonas axonopodis* pv. *allii* strains by means of a restriction profile analysis, for example using the NheI enzyme which cleaves only the amplification product of *Xanthomonas euvesicatorla* strains (group 9.2), or using the CfrI enzyme which cleaves only the amplification product of *Xanthomonas axonopodis* subgroup 9.1, in particular *Xanthomonas axonopodis* pv. *begoniae.*

A subject of the present invention is also a kit for detecting *Xanthomonas axonopodis* pv. *allii*, comprising one or more polynucleotide(s) in accordance with the invention capable of selectively hybridizing, under stringent conditions, with the target sequence SEQ ID NO: 6. Preferably, the detection kit also comprises one or more polynucleotide(s) capable of selectively hybridizing, under stringent conditions, the target sequence SEQ ID NO: 5.

The present invention will be understood more clearly by means of the further description which follows, which refers to nonlimiting examples illustrating the implementation of the present invention for detecting *Xanthomonas axonopodis* pv. *allii.*

BRIEF DESCRIPTION OF THE DRAWINGS

FIG. 1 represents the sequence SEQ ID NO: 6. The sequence fragments in bold delimit the primers PXaa2U, PXaa2L, NXaa2U and NXaa2L.

FIG. 2 represents the sequence SEQ ID NO: 5. The sequence fragments in bold delimit the primers PXaa1U, PXaa1L, NXaa1U and NXaa1L.

EXAMPLE 1

Figure 3:
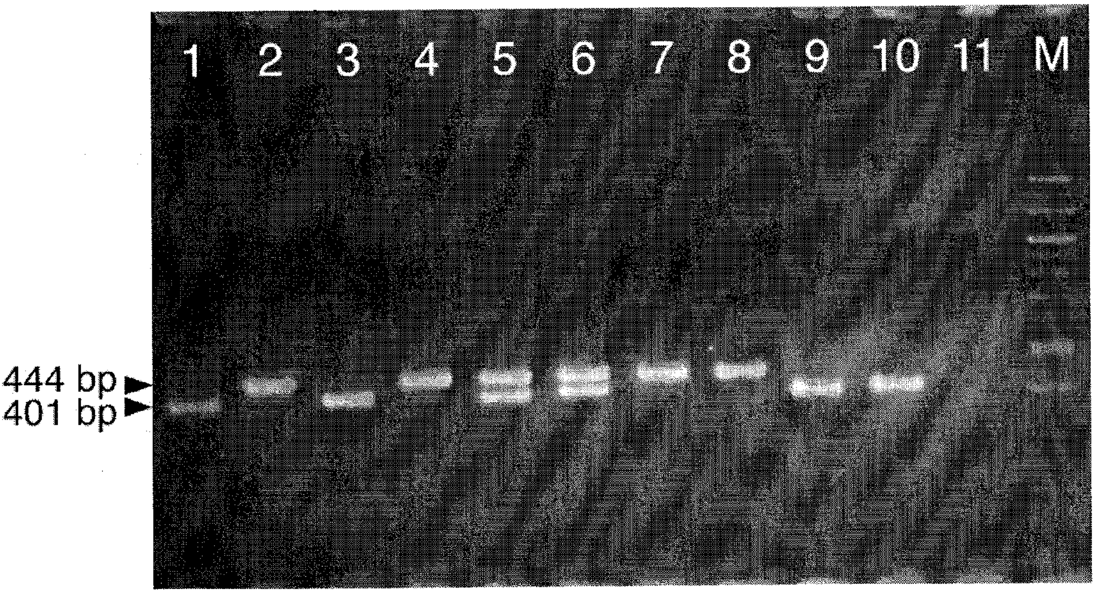
FIG. 3 shows the results of a multiplex nested PCR. Lane 11 represents the negative PCR control, lanes 1 to 10 represent the results obtained for the strains CFBP 6384, CFBP 6385, CFBP 6380, CFBP 6379, CFBP 6369, CFBP 6107, JY 276, CFBP 6387, CFBP 6368 and CFBP 6381. Lane M corresponds to the molecular size markers.

Identification of the "PIL" and "AVR" Markers 1.1. Identification of the "PIL" Marker The strains used in the present study were cultured on YPGA medium (7 $g \cdot l^{-1}$ of yeast extract, 7 $g \cdot l^{-1}$ of peptone, 7 $g \cdot l^{-1}$ of glucose, 18 $g \cdot l^{-1}$ of agar, pH 7.2) or on modified Wilbrink medium (10 $g \cdot l^{-1}$ sucrose, 5 $g \cdot l^{-1}$ bactopeptone, 5 $g \cdot l^{-1}$ of yeast extract, 0.5 $g \cdot l^{-1}$ of $K_2HPO_4$, 0.25 $g \cdot l^{-1}$ of $MgSO_4/7H_2O$, 0.05 $g \cdot l^{-1}$ of $Na_2SO_3$, 15 $g \cdot l^{-1}$ of agar, pH 6.9-7; Rott et al., Agron. Trop.; 43: 244-251, 1988) for the strains showing weak growth on the YPGA medium.

Random amplification of polymorphic DNA, or RAPD, was then carried out. For this, the total DNA of twenty-two *Xanthomonas axonopodis* pv. *allii* strains originating from various geographic regions (cf. below, table I, the strains labeled with "[b]") and of six other *Xanthomonas* (cf. below, table II, the strains labeled "[d]") was extracted from 2 ml of bacterial culture using the "DNeasy blood and tissue" kit (Qiagen, Courtaboeuf, France) according to the supplier's instructions.

A PCR amplification was carried out on the DNA extracts resulting from each strain. The reaction medium of 25 μl contains 25 ng of bacterial genomic DNA, 3 mM of $MgCl_2$, 0.4 μM of primers, 2.5 units of Taq DNA polymerase (Invitrogen, Merelbeke, Belgium), 100 μM of each of the dNTPs (Roche Diagnotics, Meylan, France) in 20 mM Tris-HCl medium and 50 mM of KCl buffer (pH 8.4). About a hundred short primers of 10 nucleotides of arbitrarily defined sequence, originating from the 80, 70 and 60% GC kits (Genome Express, Meylan, France), were tested.

The amplification was carried out under the following conditions:

- initial denaturation at 94° C. for 7 min,
- 40 amplification cycles each comprising 3 phases: 94° C. for 1 min (denaturation), 35° C. for 1 min (hybridization of the primers on the DNA) and 72° C. for 2 min (polymerization),
- extension at 72° C. for 5 min.

The amplification products were subjected to 2% NuSieve agarose gel electrophoresis and visualized by fluorescence after staining with ethidium bromide.

It was found that none of the fragments was present in all of the *Xanthomonas axonopodis* pv. *allii* strains tested and absent from the other pathovars. Among the amplified fragments found in most of the *Xanthomonas axonopodis* pv. *allii* strains and absent from the other strains, the fragment amplified with the primer called 80-21 (SEQ ID NO: 11; 5' ACGCGCCAGG 3'), of approximately 940 bp, is present in 70% of the *Xanthomonas axonopodis* pv. *allii* strains tested.

This fragment of interest was excised from the agarose gel for the *Xanthomonas axonopodis* pv. *allii* strains CFBP6364, CFBP6366, CFBP6369 and CFBP6379, extracted using the "QIAquick gel Extraction" extraction kit (Qiagen, Courtaboeuf, France), and then cloned by ligation into the pGEM-T Easy vector according to the supplier's instructions (Promega, Madison, USA). The sequence was then determined by sequencing using the T7 and SP6 primers, which hybridize to the regions bordering the insert cloned into the pGEM-T Easy vector. This fragment is 99% identical between these four strains, and a search in the GenBank database reveals that it shares 97% identity with two contiguous portions (respectively of 828 and 102 bp) belonging to the PILW and PILX genes of *Xanthomonas euvesicatoria*, which genes encode pilus assembly proteins.

It should be noted that none of the other fragments identified by RAPD were present in the strains of which the genome was not amplified by the 80-21 primer.

1.2. Identification of the "AVR" Marker

The *Xanthomonas axonopodis* pv. *allii* strains CFBP6369, CFBP6380, CFBP6384, JX36-1, CFBP6386 and CFBP6382, representative of the strains not amplified by the 80-21 primer, were analyzed using the AFLP technique. A *Xanthomonas citri* pv. *ciuri* strain (IAPAR 306) and a *Xanthomonas campestris* pv. *campestris* strain (CFBP 5251) were used as control.

The AFLP analysis was carried out as described by Ah-You et al. (International Journal of Systematic and Evolutionary Microbiology, 59: 306-318, 2009).

The bacterial DNA, extracted as previously indicated, was digested jointly with SacI and MspI, and then ligation with the SacI and MspI linkers was carried out for 3 hours at 37° C. by adding 2.5 μl of digestion product to 22.5 μl of a ligation mixture containing 2 μM of the MspI linker, 0.2 μM of the SacI linker (Applied Biosystems, Courtaboeuf, France) and 2 units of T4 DNA ligase (New England Biolabs Ozyme) in 1× ligation buffer. A PCR preamplification is carried out in 15 μl of reaction mixture consisting of 5 μl of the ligation mixture diluted to 1/10th, 2.5 mM of $MgCl_2$, 0.23 μM of each of the primers PSAC (SEQ ID NO: 12) and PMSP (SEQ ID NO: 13), 0.45 μM of each dNTP, and 0.5 unit of Taq DNA polymerase (Goldstar Red, Eurogentec, Seraing, Belgium) in a 1× Goldstar buffer. The amplification was carried out under the following conditions:

- initial extension at 72° C. for 2 min,
- initial denaturation at 92° C. for 2 min,
- 25 amplification cycles, each comprising 3 phases: 94° C. for 30 sec (denaturation), 56° C. for 30 sec (hybridization of the primers on the DNA) and 72° C. for 2 min (polymerization),
- extension at 72° C. for 10 min.

The amplification products are then diluted 10-fold in HPLC water, before the selective amplification. The selective amplification is carried out using the pairs of unlabeled primers MspI (SEQ ID NO: 14)+A, T, G or C and SacI+C (SEQ ID NO: 15), or MspI (SEQ ID NO: 14)+A, T, G or C and SacI+CT (SEQ ID NO: 16). The amplification conditions are the same as those described for the preamplification, with the exception of the concentration of the primers SacI+C and SacI+CT, which is 0.12 μM.

The amplification products were then analyzed on a 5% acrylamide gel (Risterucci et al., Theor. Appl. Genet.; 101: 948-955, 2000) and then the DNA was visualized by silver staining (Qu et al., Electrophoresis; 26: 99-101, 2005). Owing to the complexity of the AFLP profiles obtained using two selective bases in the amplification step, only the profiles obtained with three selective bases were exploited for recovering the fragments of interest.

Two fragments present in the majority of the *Xanthomonas axonopodis* pv. *allii* strains, including the strains which are not amplified by the 80-21 primer, were visualized.

In order to identify these fragments, the DNA was extracted from the acrylamide gel in 50 μl of buffer. 5 μl were then subjected to selective amplification, as described by Ah-You et al. (International Journal of Systematic and Evolutionary Microbiology, 59: 306-318, 2009), using the pairs of primers MspI (SEQ ID NO: 14)+A or T and SacI+CT (SEQ ID NO: 16). The amplification conditions are the same as those described for the preamplification, with the exception of the concentration of the primer SacI+CT, which is 0.12 μM.

The amplified fragments were then introduced by ligation into the pGEM-T Easy vector as described above, and then *E. coli* bacteria were transformed with the vectors containing the inserts. Despite the more stringent conditions for amplification with three selective bases, the sequencing of the clones obtained revealed that the DNAs had a heterogeneous composition, which is no doubt explained by a comigration of amplification products of similar size or a contamination during the excision step. Nevertheless, using the amplification with three selective nucleotides, an interesting clone was obtained from the AFLP fragments originating from the CFBP 6382 strain. Sequencing of the insert of this clone followed by a search in the GenBank database revealed the presence of a 270 bp sequence having 90% identity with a portion of the avrRxv avirulence gene of *Xanthomonas euvesicatoria* (GenBank accession number L20423). On the basis of this sequence, the primers F1154 (SEQ ID NO: 17) and R1391 (SEQ ID NO: 18) were generated and then a PCR was carried out using these primers on the strains CFBP6366, CFBP6380, CFBP6384, JX36-1, CFBP 6386, CFBP6357 and CFBP6382.

The PCR amplification was carried out in 25 μl of reaction mixture consisting of 20 ng of total DNA, 3 mM of $MgCl_2$, 0.2 μM of primers, 1.25 units of Dap Goldstar polymerase (Eurogentec, Seraing, Belgium), and 100 μM of each of the dNTPs (Roche Diagnotics, Meylan, France). The following amplification conditions were used:

- initial extension at 72° C. for 2 min,
- initial denaturation at 94° C. for 5 min, 40 amplification cycles, each comprising 3 phases: 95° C. for 1 min (denaturation), 60° C. for 1 min (hybridization of the primers on the DNA) and 72° C. for 2 min (polymerization), extension at 72° C. for 5 min.

An amplicon of 238 bp was obtained for each of the strains tested: depending on the strains, the 238 bp fragment shared 90 to 99% of the avrRxv avirulence gene of *Xanthomonas euvesicatoria* (GenBank accession number L20423). In order to obtain larger DNA fragments so as to design PCR primers specific for *Xanthomonas axonopodis* pv. *allii*, amplifications were carried out using the pair of primers F202 (SEQ ID NO: 19), corresponding to nucleotides 202-219 of the avrRxv avirulence gene of *Xanthomonas euvesicatoria* (GenBank accession number L20423) and R1391 (SEQ ID NO: 18) chosen in the 238 bp amplicon, and also the pair of primers F1154 (SEQ ID NO: 17) and R2149 corresponding to nucleotides 2131-2149 (SEQ ID NO: 20) of the avrRxv avirulence gene of *Xanthomonas euvesicatoria* (GenBank accession number L20423). A fragment of 1948 bp was amplified for the strains CFBP6366, CFBP6386, CFBP6357 and CFBP6382, a fragment of 1950 bp for the strains CFBP 6384 and JX36-1, and a partial sequence of 1504 bp for the strain CFBP 6380. All these sequences exhibit between 87 and 98% identity with the avrRxv gene of *Xanthomonas euvesicatoria*.

EXAMPLE 2

Specific Detection of *Xanthomonas Axonopodis* Pv. *Allii*

2.1. Specificity of the Detection by Multiplex Nested PCR

Pairs of primers were designed, on the basis of the "PIL" (SEQ ID NO: 5) and "AVR" (SEQ ID NO: 6) markers, by selecting the most conserved regions of these two markers among the *Xanthomonas axonopodis* pv. *allii* strains.

For the "PIL" marker, the two pairs of primers chosen are the pair of primers PXaa1U (SEQ ID NO: 1) and PXaa1L (SEQ ID NO: 2), and the pair of primers NXaa1U (SEQ ID NO: 3) and NXaa1L (SEQ ID NO: 4).

For the "AVR" marker, the two pairs of primers chosen are the pair of primers PXaa2U (SEQ ID NO: 7) and PXaa2L (SEQ ID NO: 8), and the pair of primers NXaa2U (SEQ ID NO: 9) and NXaa2L (SEQ ID NO: 10).

An analysis by multiplex nested PCR was then carried out using these four pairs of primers on 87 *Xanthomonas axonopodis* pv. *allii* strains (cf. table I hereinafter), 101 phytopathogenic bacterial strains (other pathovars and species of *Xanthomonas*, other bacterial genera), and 18 saprophytic bacteria from onion (cf. table II hereinafter).

Various types of samples were tested, in particular purified bacterial genomic DNA, bacterial suspensions and seeds mixed with a bacterial strain.

The first step of the analysis by multiplex nested PCR was carried out in a reaction mixture of 25 μl consisting of 0.5 to 5 μl of test sample (depending on the type of sample), 3 mM of $MgCl_2$, 0.2 μM of each of the primers constituting the pairs of primers PXaa2U (SEQ ID NO: 7)/PXaa2L (SEQ ID NO: 8) and PXaa1U (SEQ ID NO: 1)/PXaa1L (SEQ ID NO: 2), 100 μM of each dNTP, 1.25 units of Taq DNA polymerase (Goldstar Red, Eurogentec, Seraing, Belgium), in a 75 mM Tris-HCl buffer containing 20 mM $(NH_4)_2SO_4$ and 0.01% Tween 20 (pH 8.8).

The amplification conditions used were the following:

initial denaturation at 94° C. for 5 min, 40 amplification cycles, each comprising 3 phases: 95° C. for 1 min (denaturation), 63° C. for 1 min (hybridization of the primers on the DNA) and 72° C. for 2 min (polymerization), extension at 72° C. for 5 min.

The second step of the multiplex nested PCR was carried out with I to 5 μl of the amplicons obtained in the first amplification step, under conditions analogous to those described for the first amplification step, with the exception of the pairs of primers, which are the following: NXaa2U (SEQ ID NO: 9)/NXaa2L (SEQ ID NO: 10) and NXaa1U (SEQ ID NO: 3)/NXaa1L (SEQ ID NO: 4) were used. The amplification program was the following:

initial denaturation at 95° C. for 5 min, 30 amplification cycles, each comprising 3 phases: 94° C. for 30 sec (denaturation), 57° C. for 30 sec (hybridization of the primers on the DNA) and 72° C. for 40 sec (polymerization), extension at 72° C. for 5 min.

The amplification products were then analyzed on a 1% agarose gel (amplicon originating from the first amplification step) or a 3% agarose gel (amplicon originating from the second amplification step).

Among the 87 *Xanthomonas axonopodis* pv. *allii* strains tested, three types of results are obtained during the first amplification step:

i) two amplicons having the expected sizes, 694 bp (a portion of the "PIL" marker) and 995 bp (a portion of the "AVR" marker), were amplified from all the strains from Brazil, Cuba, Japan, Mauritius, Reunion Island and Hawaii;

ii) a single amplicon of 694 bp (a portion of the "PIL" marker) was amplified from all the strains originating from Georgia and from Venezuela, from four strains from Colorado and from two strains originating from South Africa;

iii) a single amplicon of 995 bp (a portion of the "AVR" marker) was amplified from all the strains originating from Barbados and from Texas, three strains originating from South Africa and one originating from Colorado.

During the second amplification step, the following fragments, resulting from the internal amplification of the amplification products from the first step, were observed: two fragments of 444 bp (an internal portion of the "PIL" amplicon) and 401 bp (an internal portion of the "AVR" amplicon) were obtained for the group exhibiting profile i), and a single amplicon of 444 and 401 bp, respectively, was obtained for groups ii) and iii).

The results obtained for the 87 *Xanthomonas axonopodis* pv. *allii* strains tested are summarized in table I below.

In addition, the pathogenicity of these 87 strains was confirmed by verification of Koch's postulates using, for each strain, the host species from which it originates.

TABLE I

| Strains[a] | Origin | Host | Response in multiplex nested PCR[f] 694 bp/444 bp amplicons (PIL marker) | 995 bp/401 bp amplicons (AVR marker) |
|---|---|---|---|---|
| CFBP 6384[bdeh], JX36-1[dehi], CFBP 6386[bdehi] | South Africa | *A. cepa* L | −/− | +/+ |
| CFBP 6385[bg], JX36-2[j] | South Africa | *A. cepa* L | +/+ | −/− |
| CFBP 6367[bh], JR512[i], JR513[hi], JR514, JR515, CFBP 6368[hi] | Barbados | *A. cepa* L | −/− | +/+ |
| CFBP 6362[bgh], CFBP 6363[gh], JV593[gh], CFBP 6377[ghj] | Brazil | *A. cepa* L | +/+ | +/+ |
| CFBP 6378[b] | Brazil | *A. cepa* L | −/− | +/+ |
| CFBP 6364[begh], CFBP 6365[gh] | Cuba | *A. sativum L* | +/+ | +/+ |
| CFBP 6107*[bgh], CFBP 6108[bghj] | Japan | *A. fistulosum* L | +/+ | +/+ |
| JR649, JR650, JR651, CFBP 6374[gh], JR653, JR654-1, CFBP 6374, JR653, JR654-1, JR655, CFBP 6376[bgh], JS959, JS960, JS961, JS962 | Mauritins | *A. cepa* L | +/+ | +/+ |
| JQ740-1, LMG 16528[bghj], CFBP 6366[bceghj], CFBP 6369[bedghj], CFBP 6357[egh], JQ759, JR520-1, JR523-1, CFBP 6371[gh], CFBP 6372, CFBP 6373, CFBP 6375 | Reunion Island | *A. cepa* L | +/+ | +/+ |
| CFBP 6358[gh], LA261-18, JX366-2 | Reunion Island | *A. sativum L* | +/+ | +/+ |
| JX-373-2, LB239-18 | Reunion Island | *A. porrum L* | +/+ | +/+ |
| JY317[gi], CFBP 6379[beg], JY319[g] JY320[g] | Colorado (USA) | | +/+ | −/− |
| CFBP 6380[bdehi] | Colorado (USA) | *A. cepa* L | −/− | +/+ |
| JY274, JY275, JY276[bgi] | Georgia (USA) | | +/+ | −/− |
| LMG 577, LMG 578, LMG 579[i], CFBP 6359[bgh], LMG 943, LMG 9487, LMG 9488, LMG 9489, CFBP 6360[gh], LMG 9491, LMG 9492, CFBP 6361[bgh], LMG 9494 | Hawaii (USA) | *A. cepa* L | +/+ | +/+ |
| JW200, CFBP 6381[bhi], JW202, CFBP 6382[bde], JW204, JW205, CFBP 6383[hi] | Texas (USA) | *A. cepa* L | −/− | +/+ |
| CFBP 6387[bg], JX722[j], JX724, JX725, JX726, CFBP 6388[bg], JX728 | Venezuela | *A. cepa* L | +/+ | −/− |

[a]CFBP, French Collection of Phytopathogenic Bacteria, Plant Pathology Station, Angers, France. BCCMTM/LMG, Bacteria collection, Laboratory of Microbiology, Ghent University, Belgium; the other strains belong to our laboratory collection (3P, Reunion, France). All the strains listed in this table are pathogenic for onion.

[b]Strains used to evaluate the RAPD markers (22 strains).

[c]Strains for which the RAPD marker 80-21 was cloned and sequenced (4 strains).

[d]Strains used for evaluating the AFLP markers (6 strains).

[e]Strains for which the AFLP fragment of 238 bp was cloned and sequenced (7 strains).

[f]+, fragment of expected size amplified; −, no detectable amplicon.

[g]Strains for which the DNA was amplified by the primers PXaa1U and PXaa1L and sequenced (27 strains).

[h]Strains for which the DNA was amplified by the primers PXaa2U and PXaa2L and sequenced (28 strains).

[i]Strains used for the restriction analysis with CfrI (8 strains).

[j]Strains used for the restriction analysis with NheI (10 strains).

*Pathotype strain.

An example of a multiplex nested PCR result is illustrated in FIG. 3. Lane 11 represents the negative PCR control, lanes 1 to 10 represent the results obtained for the strains CFBP 6384, CFBP 6385, CFBP 6380, CFBP 6379, CFBP 6369, CFBP 6107, JY 276, CFBP 6387, CFBP 6368 and CFBP 6381. Lane M corresponds to the molecular size markers.

During the multiplex nested PCR tests carried out on the saprophytic strains from onion and on strains belonging to other bacterial genera, no amplification product was observed. Similarly, the majority of the *Xanthomonas* strains are not amplified by multiplex nested PCR. However, it was found that a few *Xanthomonas axonopodis* strains classified in genetic subgroup 9.2 sensu Rademaker were also detected. Depending on the pathovar, the amplicons of the "PIL" marker and/or that of the "AVR" marker are revealed. In addition, the amplicons of the "AVR" marker are also detected for the strains of *Xanthomonas axonopodis* pv. *begoniae* (genetic subgroup 9.1 sensu Rademaker).

The results obtained for the saprophytic strains from onion and the strains belonging to other bacterial genera tested are summarized in table II below.

TABLE II

| | | Response to multiplex nested PCR[e] | |
|---|---|---|---|
| Strains[a] | Taxon | 694 bp/444 bp amplicons (PIL marker) | 995 bp/401 bp amplicons (AVR marker) |
| Genetic subgroup 9.2 | | | |
| LMG 667[bdefh], LMG 668[efh], LMG 905[h], LMG 909, LMG 910[efh], LMG 913[beh], LMG 914[h], LMG 922[efh], LMG 926[e], LMG927[e], LMG 929[efh], LMG 930[ef], LMG 931[efh], LMG 932[efh], LMG 933[efh], CFBP 5600*[efh] | *Xanthomonas euvesicatoria* | +/+ | +/+ |
| JJ238-20, JJ238-26, JJ238-27, JJ238-28 | *Xanthomonas axonopodis* pv. *citrumelo* | −/− | −/− |
| CFBP 2910[bf] | *Xanthomonas axonopodis* pv. *citrumelo* | −/− | +/+ |
| LMG 497[d]*, LMG 8019 | *Xanthomonas axonopodis* pv. *alfalfae* | −/− | −/− |
| LMG 675[d]* | *Xanthomonas axonopodis* pv. *cassiae* | −/− | −/− |
| LMG 8048[be] | *Xanthomonas axonopodis* pv. *cassavae* | +/+ | −/− |
| LMG 861[d]* | *Xanthomonas axonopodis* pv. *ricini* | −/− | −/− |
| LMG 686* | *Xanthomonas axonopodis* pv. *coracanae* | −/− | −/− |
| LMG 691* | *Xanthomonas axonopodis* pv. *cyamopsidis* | −/− | −/− |
| LMG 692[bf]* | *Xanthomonas axonopodis* pv. *desmodii* | −/− | +/+ |
| LMG 693[be]* | *Xanthomonas axonopodis* pv. *desmodiigangetici* | +/+ | −/− |
| LMG 694* | *Xanthomonas axonopodis* pv. *desmodiirotundifolii* | −/− | −/− |
| LMG 698* | *Xanthomonas axonopodis* pv. *erythrinae* | −/− | −/− |
| LMG 811* | *Xanthomonas axonopodis* pv. *patelii* | −/− | −/− |
| LMG 844[bef]* | *Xanthomonas axonopodis* pv. *phyllanthi* | +/+ | +/+ |
| LMG 849* | *Xanthomonas axonopodis* pv. *poinsettiicola* | −/− | −/− |
| LMG 955*[c] | *Xanthomonas axonopodis* pv. *tamarindi* | +/+ | −/− |
| NCPPB 938[bef] | *Xanthomonas axonopodis* pv. *lespadecae* | +/+ | +/+ |
| Genetic subgroup 9.1 | | | |
| LMG 551[bfg], LMG 7303[bfg]*, CFBP 2524[bfg] | *Xanthomonas axonopodis* pv. *begoniae* | +/+ | +/+ |
| Genetic subgroup 9.3 | | | |
| LMG 982*, LMG 539 | *Xanthomonas axonopodis* pv. *axonopodis* | −/− | −/− |
| LMG 901*, LMG 8285 | *Xanthomonas axonopodis* pv. *vuscalorum* | −/− | −/− |
| Genetic subgroup 9.4 | | | |
| LMG 8014, JR518-3 | *Xanthomonas axonopodis* pv. *phaseoli* | −/− | −/− |
| CFBP 2603 | *Xanthomonas axonopodis* pv. *manihotis* | −/− | −/− |

TABLE II-continued

| Strains[a] | Taxon | Response to multiplex nested PCR[e]: 694 bp/444 bp amplicons (PIL marker) | Response to multiplex nested PCR[e]: 995 bp/401 bp amplicons (AVR marker) |
|---|---|---|---|
| LMG 695[d]* | *Xanthomonas axonopodis* pv. *dieffenbachiae* | −/− | −/− |
| Genetic subgroup 9.5 | | | |
| C 39, JA159-1, CFBP 2525[d]*, IAPAR 306 | *Xanthomonas axonopodis* pv. *citri* | −/− | −/− |
| LMG 548* | *Xanthomonas axonopodis* pv. *bauhiniae* | −/− | −/− |
| LMG 558* | *Xanthomonas axonopodis* pv. *cajani* | −/− | −/− |
| CFBP 1716*, CFBP 2933 | *Xanthomonas axonopodis* pv. *mangiferaeindicae* | −/− | −/− |
| LMG 761*, LMG 7429 | *Xanthomonas axonopodis* pv. *malvacearum* | −/− | −/− |
| Genetic subgroup 9.6 | | | |
| LMG 7387 | *Xanthomonas axonopodis* pv. *cajani* | −/− | −/− |
| LMG 8752* | *Xanthomonas axonopodis* pv. *vignicola* | −/− | −/− |
| Other species | | | |
| LMG 733, CFBP 4925† | *Xanthomonas hortorum* pv. *hederae* | −/− | −/− |
| LMG 904, LMG 915, LMG 911† | *Xanthomonas vesicatoria* | −/− | −/− |
| CFBP 1156† | *Xanthomonas hyacinthi* | −/− | −/− |
| CFBP 1976† | *Xanthomonas bromi* | −/− | −/− |
| LMG 710, CFBP 2157† | *Xanthomonas fragariae* | −/− | −/− |
| CFBP 5251† | *Xanthomonas campestris* pv. *campestris* | −/− | −/− |
| CFBP 2528† | *Xanthomonas arboricola* pv. *juglandis* | −/− | −/− |
| CFBP 2532† | *Xanthomonas oryzae* pv. *oryzae* | −/− | −/− |
| CFBP 2542† | *Xanthomonas cucurbitae* | −/− | −/− |
| CFBP 2543† | *Xanthomonas vasicola* pv. *holcicola* | −/− | −/− |
| CFBP 4188† | *Xanthomonas cynarae* | −/− | −/− |
| CFBP 4641† | *Xanthomonas sacchari* | −/− | −/− |
| LMG 673† | *Xanthomonas cassavae* | −/− | −/− |
| CFBP 4644† | *Xanthomonas melonis* | −/− | −/− |
| CFBP 4643† | *Xanthomonas pisi* | −/− | −/− |
| CFBP 4690† | *Xanthomonas codia* | −/− | −/− |
| CFBP4691† | *Xanthomonas theicolo* | −/− | −/− |
| CFBP 2523† | *Xanthomonas albilineans* | −/− | −/− |
| LMG 797* | *Xanthomonas oryzae* pv. *oryzicola* | −/− | −/− |
| LMG 892* | *Xanthomonas translucens* pv. *undulosa* | −/− | −/− |
| LMG 471* | *Xanthomonas sacchari* | −/− | −/− |
| Other phytopathogenic bacteria | | | |
| LMG 1222† | *Burkholderia cepatia* | −/− | −/− |
| CFBP 2094 | *Pseudomonas savastanoi* pv. *savastanoi* | −/− | −/− |
| CFBP1670† | *Pseudomonas savastanoi* | −/− | −/− |
| Run 145 | *Ralstonia solanacearum* phylotype III | −/− | −/− |
| Run 215 | *Ralstonia solanacearum* phylotype I | −/− | −/− |
| Run 17 | *Ralstonia solanacearum* phylotype II | −/− | −/− |
| Run 83 | *Ralstonia solanacearum* phylotype IV | −/− | −/− |
| LMG 1199† | *Ralstonia eutropha* | −/− | −/− |
| LMG 2172† | *Pseudomonas corrugata* | −/− | −/− |
| LMG 5093* | *Pseudomonas syringae* pv. *tomato* | −/− | −/− |
| LMG 5942† | *Ralstonia pickettii* | −/− | −/− |
| LMG 1794† | *Pseudomonas fluorescens* | −/− | −/− |
| LMG 16206† | *Pseudomonas putida* | −/− | −/− |
| LMG 2162† | *Pseudomonas cichorii* | −/− | −/− |

TABLE II-continued

| Strains[a] | Taxon | Response to multiplex nested PCR[e] 694 bp/444 bp amplicons (PIL marker) | 995 bp/401 bp amplicons (AVR marker) |
|---|---|---|---|
| LMG 2129 | *Burkholderia andropogonis* | −/− | −/− |
| LMG 2804† | *Erwinia chrysanthemi* | −/− | −/− |
| Saprophytic strains isolated from onion | | | |
| JS923, JS924 | *Erwinia* sp. | −/− | −/− |
| JR593 | *Burkholderia* sp. | −/− | −/− |
| JR594-1 | *Stenotrophomonas* sp. | −/− | −/− |
| JR594-2 | *Pseudomonas* sp. | −/− | −/− |
| JR656-3 | *Klebsiella* sp. | −/− | −/− |
| JR656-5 | *Pantoea* sp. | −/− | −/− |
| JR656-6 | *Pantoea* sp. | −/− | −/− |
| JS741-1 | *Burkholderia* sp. | −/− | −/− |
| JS741-2, JS741-4, JS741-12 | *Flavimonas oryzihabitans* | −/− | −/− |
| JS741-5 | *Klebsiella* sp. | −/− | −/− |
| JS741-6 | *Pantoea agglomerans* | −/− | −/− |
| JS853 | *Pantoea* sp. | −/− | −/− |
| JS741-14 | *Enterobacter* sp. | −/− | −/− |
| JS741-15, JS741-16 | *Pseudomonas aeruginosa* | −/− | −/− |

[a]CFBP, French Collection of Phytopathogenic Bacteria, Plant Pathology Station, Angers, France: BCCMTM/LMG, Bacteria collection, Laboratory of Microbiology, Ghent University, Belgium; NCPPB, the National Collection of Plant Pathogenic Bacteria (NCPPB, CSL, York, United Kingdom); the other strains belong to our laboratory collection (3P, Reunion, France), except for the strain IAPAR 306 which was provided by the IAPAR (Instituto Agronomico do Parana [Agronomic Institute of Parana], Londrina PR, Brazil) and for which the complete genome is available (Da Silva, 2002). All the strains listed in this table are pathogenic for onion.

[b]Strains used for the tests for pathogenicity on onion (*Allium cepa* L., cv. Red Creole).

[c]+, amplified fragment of the expected size; −, no amplicon detected.

[d]Strains used to evaluate the RAPD markers (6 strains).

[e]Strains for which the DNA was amplified by the primers PXaa1U and PXaa1L and sequenced (18 strains).

[f]Strains for which the DNA was amplified by the primers PXaa2U and PXaa2L and sequenced (17 strains).

[g]Strains used for the restriction analysis with CfrI (3 strains).

[h]Strains used for the restriction analysis with NheI (12 strains).

†Type strain.

*Pathotype strain.

Pathogenicity tests were carried out for all the strains of table II, using the onion cultivar Red Creole (Roumagnac et al., Eur. J. Plant Pathol., 106: 867-877, 2000). These tests showed that although they are detected by multiplex nested PCR, none of the strains that do not belong to the *allii* pathovar are pathogenic to onion. In addition, said strains can easily be distinguished from the *Xanthomonas axonopodis* pv. *allii* strain by restriction profile analysis. Indeed, analysis of the amplicons obtained during the second amplification step indicates that the NheI restriction enzyme does not cleave the 444 bp fragment (amplicon of the "PIL" marker) originating from the *Xanthomonas axonopodis* pv. *allii* strain, whereas it cleaves the amplification product from the *Xanthomonas euvesicatoria* strain, generating two fragments of 355 and 89 bp, respectively. In the same way, the CfrI restriction enzyme generates two fragments of 343 and 58 bp from the 401 bp amplification product (amplicon of the "AVR" marker) from *Xanthomonas axonopodis* pv. *begoniae*, whereas it does not cleave the amplicon originating from *Xanthomonas axonopodis* pv. *allii*.

2.2. Sensitivity of the Detection by Multiplex Nested PCR

The sensitivity of the method of detection by multiplex nested PCR was determined using bacterial suspensions optionally mixed with samples of onion seeds.

The suspensions of the *Xanthomonas axonopodis* pv. *allii* strains CFBP 6366, CFBP 6385 and CFBP 6367 were tested. For this, the suspensions containing $1\times10^8$ cfu·ml$^{-1}$ were serially diluted 10-fold. Samples containing 10 g of healthy onion seeds were placed in 50 ml of sterile 0.01 M Sigma 7-9 buffer (pH 7.2) (Sigma, Saint-Quentin Fallavier, France) and were inoculated with bacterial suspensions at a final concentration ranging from $1\times10^1$ cfu·ml$^{-1}$ to $1\times10^7$ cfu·ml$^{-1}$. The negative control was inoculated with buffer. In parallel, the same dilution series not mixed with the seeds were analyzed. After 48 hours of maceration at 4° C., the samples were firstly inoculated onto NCTM1 semi-selective medium (Roumagnac et al., Eur. J. Plant. Pathol.; 106: 867-877, 2000), and secondly, the bacterial genome was extracted according to the rapid alkaline extraction method of Audy et al. (Phytopathology; 86: 361-366, 1993). 4 ml of each sample were centrifuged at 10 000 g for 30 min at 4° C. and then the pellet was resuspended in 100 µl of 0.5 N NaOH containing 0.5% of polyvinylpyrrolidone. 5 µl of lysate were mixed with 495 µl of a 20 mM Tris-HCl solution, pH 8.0. For each experiment, two samples of 5 µl (for the suspensions containing at least $1\times10^6$ cfu·ml$^{-1}$) or three samples of 5 µl (for the suspensions containing less than $1\times10^4$ cfu·ml$^{-1}$) were tested in duplicate.

When the suspensions are mixed with onion seeds, the first step of the amplification makes it possible to detect $1\times10^6$ cfu·ml$^{-1}$ (titer determined with the corresponding suspensions inoculated onto NCTM1 medium). When the multiplex nested PCR is used, the limit of detection goes to approximately $1\times10^3$ cfu·ml$^{-1}$, although a signal is frequently obtained (once or twice out of three tests) with suspensions containing approximately $1\times10^2$ cfu·ml$^{-1}$. It should be noted that the equivalent tests carried out on the serial dilutions that were not mixed with onion seeds gave similar results.

These results show that it is possible to detect *Xanthomonas axonopodis* pv. *allii* in a sample of seeds from a concentration of $10^6$ bacteria/ml after the first amplification step, and from a concentration of $10^3$ bacteria/ml or even $10^2$ bacteria/ml after the second amplification step.

EXAMPLE 3

Detection of *Xanthomonas Axonopodis* Pv. *Allii* on Infected Seed Samples

The presence of *Xanthomonas axonopodis* pv. *allii* was investigated in a lot of onion seeds harvested on a contaminated experimental field (Humeau et al., Phytopathology, 96: 1345-1354, 2006). The number of samples for each experiment (35 per experiment), each consisting of 10 g of seeds, was determined according to a hypergeometric distribution in order to detect at least one contaminated seed out of 30 000 seeds (r=0.05). Each experiment was carried out in duplicate.

The seed samples were macerated in 50 ml of sterile 0.01 M Sigma 7-9 buffer (pH 7.2) for 48 hours. The level of contamination of the lot was determined, firstly, by culturing, on NCTM1 medium, pure macerated materials or macerated materials diluted to 1/10, and secondly, by means of at least two analyses of the macerated materials by multiplex nested PCRs after alkaline extraction carried out as described above. Negative controls in which the sample was replaced with water were included in the experiments.

In another series of experiments, the same lot of seeds was mixed with healthy onion seeds in a 1:1.1, 1:2 and 1:12.8 proportion, and then the levels of contamination of two, two and three independent samples of these mixtures were analyzed respectively by culturing on NCTM1 medium and multiplex nested PCR under the conditions previously indicated.

Since the nested PCR amplification method is known to produce false positives, only the samples from which the expected DNA fragments were detected at least twice are considered to be positive. In addition, the level of contamination determined from counting the dishes inoculated and the analyses by multiplex nested PCR was calculated according to the method described by Masmoudi et al. (Seed Sci. Technol.; 22: 407-414, 1994). The correlation between the levels of contamination determined by culturing or by multiplex nested PCR and the ratio of the infected seed/healthy seed dilutions was calculated by applying Pearson's correlation coefficient r (Pearson, K, Biometrika; 18: 105-117, 1926).

The results of these studies are recorded in table III below.

TABLE III

| | | | Detection by multiplex nested PCR | | Isolation on semi-selective medium | | |
|---|---|---|---|---|---|---|---|
| | | Number of seed samples | LC | Number of positive lots | LC | Number of positive lots | Number of lots detected by the 2 methods |
| Lot of seeds P2 | Test 1 | 35 | 0.00007675 | 6 | 0.00004953 | 4 | 3 |
| 1/10.00)[a] | Test 2 | 35 | 0.0001213 | 9 | 0.00001183 | 1 | 1 |
| | mean | | 0.00010 | | 0.00003068 | | |
| Lot of seeds P2 | Test 1 | 35 | 0.00003658 | 3 | 0 | 0 | 0 |
| mixed with healthy | Test 2 | 35 | 0.00004953 | 4 | 0.00002402 | 2 | 0 |
| seeds (1:1.1) | mean | | 0.000043055 | | 0.00001201 | | |
| 1/21.000[b] | | | | | | | |
| Lot of seeds P2 | Test 1 | 35 | 0.00003658 | 3 | 0 | 0 | 0 |
| mixed with healthy | Test 2 | 35 | 0.00003658 | 3 | 0.00001183 | 1 | 0 |
| seeds (1:2) | mean | | 0.00003658 | | 0.000005915 | | |
| 1/30000[b] | | | | | | | |
| Lot of seeds P2 | Test 1 | 35 | 0 | 0 | 0.00001183 | 1 | 0 |
| mixed with healthy | Test 2 | 35 | 0 | 0 | 0 | 0 | 0 |
| seeds (1:12.8) | Test 3 | 35 | 0.00003658 | 3 | 0.00001183 | 1 | 0 |
| 1/138.600[b] | mean | | 1.21933E−03 | | 0.0000079 | | |
| Healthy seeds | Test 1 | 35 | 0 | 0 | 0 | 0 | |
| Test 2 | Test 2 | 35 | 0 | 0 | 0 | 0 | |

[a]Levels of seed contamination derived from the analyses by multiplex nested PCR

[b]Theoretical levels of seed contamination obtained by diluting the seed lot P2 with healthy seeds The two methods of analysis made it possible to detect *Xanthomonas axonopodis* pv. *allii*: six and nine positive samples were respectively demonstrated by multiplex nested PCR, which corresponds to a mean level of contamination of 0.01%, whereas culturing on NCTM1 medium made it possible to detect only three and four positive samples, which corresponds to a level of contamination of 0.0031%.

The series of experiments carried out with the seed lot mixed with healthy onion seeds in a 1:1.1, 1:2 and 1:12.8 proportion, corresponding respectively to theoretical contamination levels of 1/21 000, 1/30 000 and 1/138 000, shows that the multiplex nested PCR method accurately estimates the levels of contamination: indeed, the positive correlation r between the theoretical level of contamination and the level of contamination determined experimentally by multiplex nested PCR is 0.90. Conversely, such correlation was not observed when the analysis was carried out by culturing on NCTM1 medium.

At an experimentally determined level of contamination of 1/27 300, the multiplex nested PCR is positive in each test. For higher dilutions, in particular 1/82 000, only one test out of three is positive.

Since the level of contamination recorded for epidemics of bacterial blight of onion in a tropical environment is 4.5/10 000, the detection by multiplex nested PCR, with a sensitivity threshold of the method of approximately 1/27 300, is reliable and particularly suitable for certifying Alliaceae seed lots.

The invention claimed is:

1. A method of screening for *Xanthomonas axonopodis* pv. *allii* in a biological sample derived from onion which comprises: bringing DNA of a biological sample that may contain said bacterium into contact with one or more polynucleotide(s) under conditions which allow selective hybridization between said polynucleotide(s) and the target sequence of SEQ ID NO: 6, and also with at least one polynucleotide capable of selectively hybridizing, under stringent conditions, with the target sequence of SEQ ID NO: 5; and detecting said hybridization, wherein the presence of hybridization indicates the presence of *Xanthomonas axonopodis* pv. *allii* in the biological sample.

2. A method of screening for *Xanthomonas axonopodis* pv. *allii* in a biological sample derived from onion comprising the following steps:

(i) bringing the DNA of a biological sample to be tested into contact with a pair of primers selected from the group consisting of:

(a) SEQ ID NO: 7 and 8; and (b) SEQ ID NO: 9 and 10, and under conditions which allow selective hybridization between the primers and the target sequence of SEQ ID NO: 6, and also with at least one or more polynucleotide(s) capable of selectively hybridizing, under stringent conditions, with the target sequence of SEQ ID NO: 5;

(ii) carrying out a polymerase chain reaction amplification under conditions which allow the amplification of the target sequence of SEQ ID NO: 6, and the amplification of the target sequence of SEQ ID NO: 5; and (iii) detecting the amplification product.

3. The method as claimed in claim 2, further comprising an amplification step (iv) which is a polymerase chain reaction amplification using a second pair of primers allowing the amplification of an internal fragment of the amplification product from step (ii) is carried out, in addition, in the presence of a pair of primers allowing the amplification of an internal fragment of the amplification product from the first step of amplification of the polynucleotide of sequence SEQ ID NO: 5.

4. The method as claimed in claim 3, wherein the amplification step (ii) is carried out with a pair of primers SEQ ID NO: 1 and 2 and the pair of primers SEQ ID NO: 7 and 8, and in that the amplification step (iv) is carried out with a pair of primers SEQ ID NO: 3 and 4 and the pair of primers SEQ ID NO: 9 and 10.

5. The method as claimed in claim 1, wherein the biological sample derived from onion is onion seed.

6. The method as claimed in claim 1, comprising an additional step of restriction profile analysis of the hybridized polynucleotides.

7. The method as claimed in claim 2, wherein said at least one polynucleotide capable of selectively hybridizing, under stringent conditions, with the target sequence SEQ ID NO: 5 is selected from the group consisting of SEQ ID NO: 1 to 4.

* * * * *